US007087385B2

(12) United States Patent
Kalin et al.

(10) Patent No.: US 7,087,385 B2
(45) Date of Patent: Aug. 8, 2006

(54) PROMOTER SEQUENCES FOR UROCORTIN II AND THE USE THEREOF

(75) Inventors: Ned H. Kalin, Madison, WI (US); Patrick Henry Roseboom, Madison, WI (US); Steven Anil Nanda, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 303 days.

(21) Appl. No.: 10/438,803

(22) Filed: May 15, 2003

(65) Prior Publication Data

US 2004/0002107 A1 Jan. 1, 2004

Related U.S. Application Data

(60) Provisional application No. 60/423,642, filed on Nov. 1, 2002, provisional application No. 60/381,121, filed on May 16, 2002.

(51) Int. Cl.
*C12Q 1/68* (2006.01)
(52) U.S. Cl. .......................................... 435/6
(58) Field of Classification Search ...................... None
See application file for complete search history.

(56) References Cited

U.S. PATENT DOCUMENTS 5,959,109 A 9/1999 Whitten et al.

FOREIGN PATENT DOCUMENTS

WO    WO 99/51261    10/1999

OTHER PUBLICATIONS

Reul JM, Holsboer F (2002) Corticotropin-releasing factor receptors 1 and 2 in anxiety and depression. Curr Opin Pharmacol 2:23-33.
Takahashi LK, Ho SP, Livanov V, Graciani N, Americ SP (2001) Antagonism of CRF(2) receptors produces anxiolytic behavior in animal models of anxiety. Brain Res 902:135-142.
Bakshi VP, Smith-Roe S, Newman SM, Grigoriadis DE, Kalin NH (2002) Reduction of stress-induced behavior by antagonism of corticotropin- releasing hormone 2 (CRH2) receptors in lateral septum or CRH1 receptors in amygdala. J Neurosci 22:2926-2935.
Veith RC, Lewis N, Langohr JI, Murburg MM, Ashleigh EA, Castillo S, Peskind ER, Pascualy M, Bissette G, Nemeroff CB, Raskind MA (1993) Effect of desipramine on cerebrospinal fluid concentrations of corticotropin-releasing factor in human subjects. Psychiatry Res 46:1-8.
Vaughan J, Donaldson C, Bittencourt J, Perrin MH, Lewis K, Sutton S, Chan R, Turnbull AV, Lovejoy D, Rivier C, et al. (1995) Urocortin, a mammalian neuropeptide related to fish urotensin I and to corticotropin-releasing factor. Nature 378:287-292.
Lewis K, Li C, Perrin MH, Blount A, Kunitake K, Donaldson C, Vaughan J, Reyes TM, Gulyas J, Fischer W, Bilezikjian L, Rivier J, Sawchenko PE, Vale WW (2001) Identification of urocortin III, an additional member of the corticotropin-releasing factor (CRF) family with high affinity for the CRF2 receptor. Proc Natl Acad Sci U S A 98:7570-7575.
Kozicz T, Yanaihara H, Arimura A (1998) Distribution of urocortin-like immunoreactivity in the central nervous system of the rat. J Comp Neurol 391:1-10.
Bittencourt JC, Vaughan J, Arias C, Rissman RA, Vale WW, Sawchenko PE (1999) Urocortin expression in rat brain: evidence against a pervasive relationship of urocortin-containing projections with targets bearing type 2 CRF receptors. J Comp Neurol 415:285-312.
Hsu SY, Hsueh AJ (2001) Human stresscopin and stresscopin-related peptide are selective ligands for the type 2 corticotropin-releasing hormone receptor. Nat Med 7:605-611.
Reyes TM, Lewis K, Perrin MH, Kunitake KS, Vaughan J, Arias CA, Hogenesch JB, Gulyas J, Rivier J. Vale WW, Sawchenko PE (2001) Urocortin II: A member of the corticotropin-releasing factor (CRF) neuropeptide family that is selectively bound by type 2 CRF receptors. Proc Natl Acad Sci U S A 98:2843-2848.
Million, M., et al. (2002) Am J Physiol Gastrointest Liver Physiol 282: G34-G40.
Valdez, G.R. et al. (2002) Brain Research 943: 142-150.

*Primary Examiner*—James Ketter
*Assistant Examiner*—Konstantina Katcheves
(74) *Attorney, Agent, or Firm*—Quarles & Brady, LLP

(57) ABSTRACT

Various human urocortin II promoter sequences are disclosed. Nucleic acids and host cells that contain the promoter sequences are also disclosed. Further disclosed are various methods involving the use of these sequences. Also disclosed are methods of modulating the activity of a human urocortin II promoter sequence and methods of modulating urocortin II expression in a cell.

15 Claims, 13 Drawing Sheets

SEQ ID NO:1

```
           AGGTGAGTAGGGATTCCAAGGCTTGGGTCAGAGATCGGGGTGACTTCTGT  -3478
TGTCCCTGAGGTCAGAGGTCACAGCCTGGTCCCATCTGTTGCACATAGGGGCGGCCAGGG  -3418
CCTGCCGGTCCTCGAGGCGAGAAGGGAGAAGCTGCACTGACGGTGAGTGTGGGCCTGGAT  -3358
GGGCCTGGGAGGGCCTGGGTGGGCCTGGGTGGGCTGGGGCCCTACCTCCCTCACCCAGCA  -3298
CCCTGACCCCTGGGCCCTGGCTCCATGCAGTCTCACCATAGTCCCTGTATTATGTGCCCT  -3238
ATGTCCTTCCTGTGGGCCATGGGTTCTTTATGGTCCCTGTGGTCTTCTGCTCCCAGGAGG  -3178
ATGACATCCGGGGCTTTGTGCGCCAAGAGATGAGTCAGCACTGTGGTGAGTGGTGCCCAG  -3118
CCCGCAGTCTCCCACTCCACCCCAGCACCCTAGGCAAGGGCAGGCAGGCCCCTAGAACTT  -3058
ACAGGGCAAGCAGTCAAGAAGATGGGGGGATGGATGGATACACAGAAGGACACATGTGCT  -2998
GCAGGACTGACACATGACATGTGTCCCCAGTGGAGGGAGACACACAGGCAGATGAGGATT  -2938
GCCATGCAGTGCTCTCAGATGTCCAGCTTGGCTGTGTGGGAGTGGGATGATGGTGGGAG   -2878
CAGAGCTGGTCCCCTTGGGCCTGACCTGGACCCGGTGGGAGGGGCATCAGAGTGAAGCTG  -2818
TCTCTTCCCGTCTCTGTCTGCACCACCTGCCTGTTTCTGTGTCTGGCCTGCTTCTGTCTC  -2758
TTGCCTTTTGTTGGCCTGTTCCCAACTTCCCTCTCCTCTGCCTTCTTCTCTTTTTCCATC  -2698
TCTCTATCTACCTCCCACCCTCTCTCTTCCTCTCTCTCCTGTTACCCTCTCCTGCTATCT  -2638
CTTTGTGTATCTCTACCCCTCTGCCTGTGTGTCTCTGTCTGTCTCTCCATCTTCCCATCC  -2578
TTCTCTCTGTCATTGTCTCTCTATCCCTCTCTGCCCCTCTAGCCTGCCAGGGCCAGTTC   -2518
ATCGCATCTGGATCACGTGAGTAGTTTTCTACTCCCAGAACTTTCTTCACCCCAGGCCCT  -2458
GCCCTGCCTATCAACTGGGGTCCTCTCAGGGGGGTTGGCTGGGATGGCTGCCCATGGTGA  -2398
CTTCAGGGCCCTGAGGCCCCTGCTCTTGGCTCCAGGACCCCTCCCTAGTTATGCTGCAGA  -2338
CACTGCCGGCTCCCAGCTCCATGCTGTGCCTGTGCTCCGCGTCTCTCATGCAGAGGAGGA  -2278
AGGTGAGGACAGCTGAACCCGTGGGGCAGCTATGGGTGGGGCCGAGACACGCACATGGT   -2218
GTCCATGAATGCAGGGCACACGCCAAGCACGTAGGGTCTGCATGCAGGGCACACGCATGG  -2158
GCACTGTGTGCACACAGTGGAAATCAGTGCTGCCCACCTTGCCCCGGGGCCAGCAGCCAC  -2098
```

Fig. 1

```
TGCTCCCAGCACACCCTGCCCTACCTGCAGAGCGGGTACCCCTGAGGATGATGAGTACT    -2038

CTGAATACTCCGAGTATTCTGTGGAGGAGTACCAGGACCCTGAAGCTCCTTGGGATAGTG   -1978

ATGGTGAGAATGGGGGGCTGCGCCCAGCGGGGTCTGGGGAGGGGCAGGCAGGGCTGAGCC   -1918

CTGCTGACCTCCCCCTGACCTTTCAACCCTCTCTGATTCCCACAAACCCTGCTGACTTGA   -1858

CCCCATTGGCCCAGACCCCTGTTCCCTGCCACTGGATGAGGGCTCCTGCACTGCCTACAC   -1798

CCTGCGCTGGTACCATCGGGCTGTGACAGGCAGCACAGAGGCCTGTCACCCTTTTGTCTA   -1738

TGGTGGCTGTGGAGGGAATGCCAACCGTTTTGGGACCCGTGAGGCCTGCGAGCGCCGCTG   -1678

CCCACCCCGGGTGGTCCAGAGCCAGGGGACAGGTATGGGCTGAGCCCCCACCGTGGGGAA   -1618

CTGGGCACTGAGCCTGCCTGGATCGGGTTCTGGGGGAGGAGTCCTTGGGCCAGGGTTCCA   -1558

GGTCAGGGTCCTGGAGGAGACGCTCCCTCGCAGTAGGGGACCTGGGGCAGACGCCCAGAC   -1498

CAAAGAGCTGAATATAGAGCCCCAGCCGTGGAGCCCCCAGTAGGGTCCCCTTCCATGTTC   -1438

CCTCCTTTAAAGACCTAAGTATGGACCCCTCTGAGGTCAGAGCCCCCACTTCCTGTTGTA   -1378

GCCTCCGCTCCCTCCCCTTGGCGGTGCCTCTGCCTGAGCGTCTCCGGGGAAGGTCAGATG   -1318

GCTGACGACCGTTTCCAACCTGTCCTCACCAGGTACTGCCCAGGACTGAGGCCCAGATAA   -1258

TGAGCTGAGATTCAGCATCCCTGGAGGAGTCGGGGTCTCAGCAGAACCCCACTGTCCCT   -1198

CCCCTTGGTGCTAGAGGCTTGTGTGCACGTGAGCGTGCGTGTGCACGTCCGTTATTTCAG   -1138

TGACTTGGTCCCGTGGGTCTAGCCTTCCCCCCTGTGGACAAACCCCCATTGTGGCTCCTG   -1078

CCACCCTGGCAGATGACTCACTGTGGGGGGTGGCTGTGGGCAGTGAGCGGATGTGACTG   -1018

GCGTCTGACCCGCCCCTTGACCCAAGCCTGTGATGACATGGTGCTGATTCTGGGGGGCAT   -958

TAAAGCTGCTGTTTTAAAGGCTCCTGTTGTGACTGTTTGGGAAGATGGGGGGTTTCAAG   -898

GGGGAAGGTTTTCCTTGGGGGGTTGGTATTATTCTGCATGGGTACAGAGTCCCTCTGCCC   -838

AGTCCTGGTCACTGTCTTGTGATTCTCAGTCCCCAACTTGTCCCCGGAAAAGAGTAGATA   -778

GGGTGGGGGCTAAGGACACCCCGGGAGGGATGAGTCATAGGTGGGGGGCTGCCTCATGC   -718

CAGGAAGCATGTACCAGCTCCCACCCCAGGGGGCTGAGGGAGATAAATGGGCCCTGAAGC   -658
```

Fig. 1 (continued)

```
GGGGTAGAGGGTCAGACCACAGGACAGTAGTGCCTGGCCCCAGCCCCAGGCAGCCACAGC  -598
AGGCTGCCTTACCCCAGAAGCAGCTGGTGGCGGTAGGACTGGGTTGGGTCGGGATGGGAA  -538
GGGTCTTGGAGGTTGAGTGGATGTGGGGTTTGGCTTTATGGAGGGCTTGGACCCAGGGGA  -478
CTCTGGGATCTCTGGCTGCTTTTCTGCCTCTGAGATCCGATTCCTGCCCTTCTGTTTCCT  -418
GGATCAGCTGCAAGCTCTCCTGCTGAGAACCGCCTGCCCTCCTGTGGACTCTGTGTTTCT  -358
GTCTGAATCTTTCTTTCCATCATGCTGTCTGTCTCTGGGATGGTTTCTGTCTGTCTTTTT  -298
CTTCTAGTCTCCATTTTGCTCTGCCTCCATCTCCTTCATCTCCCTCTCTTGCTGTCCCTC  -238
TGTCTCTGGATTTCTTTGTTTCTTTTTTCTGTCTTGCTTTCTGCCTCTTTGTCTCATTC  -178
TGGCTCTCCTCTTGTCTCCCCTTCTCTGTCTCTGGCCTGGCCTGGCCTCTCTAACCCCTT  -118
TCTCGGTGTCTTCCTCTCTCTCCATCCCCCGCTCTGTCACTCTGCCCTTGCCATCTGTCT  -58
                                                          ↓
CTGTCCATGGACCCCAGTTGACCAGAGCCCCTGCCCTGAGCCCATTTTCTCCTTGCAGCC  +3
```

Fig. 1 (continued)

SEQUENCE LISTING

```
<160> NUMBER OF SEQ ID NOS: 1

<210> SEQ ID NO 1
<211> LENGTH: 3530
<212> TYPE: DNA
<213> ORGANISM: Homo sapiens

<400> SEQUENCE: 1
aggtgagtag ggattccaag gcttgggtca gagatcgggg tgacttctgt tgtccctgag      60
gtcagaggtc acagcctggt cccatctgtt gcacataggg gcggccaggg cctgccggtc     120
ctcgaggcga gaagggagaa gctgcactga cggtgagtgt gggcctggat gggcctggga     180
gggcctgggt gggcctgggt gggctggggc cctacctccc tcacccagca ccctgacccc     240
tgggccctgg ctccatgcag tctcaccata gtccctgtat tatgtgccct atgtccttcc     300
tgtgggccat gggttcttta tggtccctgt ggtcttctgc tcccaggagg atgacatccg     360
gggctttgtg cgccaagaga tgagtcagca ctgtggtgag tggtgcccag cccgcagtct     420
cccactccac cccagcaccc taggcaaggg caggcaggcc cctagaactt acagggcaag     480
cagtcaagaa gatgggggga tggatggata cacagaagga cacatgtgct gcaggactga     540
```

-continued

| | |
|---|---|
| cacatgacat gtgtccccag tggagggaga cacacaggca gatgaggatt gccatgcagt | 600 |
| gctctcagat gtccagcttg gctgtgtggg gagtgggatg atggtgggag cagagctggt | 660 |
| cccttgggc ctgacctgga cccgtggga ggggcatcag agtgaagctg tctcttcccg | 720 |
| tctctgtctg caccacctgc ctgtttctgt gtctggcctg cttctgtctc ttgccttttg | 780 |
| ttggcctgtt cccaacttcc ctctcctctg ccttcttctc tttttccatc tctctatcta | 840 |
| cctcccaccc tctctcttcc tctctctcct gttaccctct cctgctatct ctttgtgtat | 900 |
| ctctacccct ctgcctgtgt gtctctgtct gtctctccat cttcccatcc ttctctctgt | 960 |
| cattgtctct ctatccctct ctgcccctc tagcctgcca gggccagttc atcgcatctg | 1020 |
| gatcacgtga gtagttttct actcccagaa ctttcttcac cccaggccct gccctgccta | 1080 |
| tcaactgggg tcctctcagg ggggttggct gggatggctg cccatggtga cttcagggcc | 1140 |
| ctgaggcccc tgctcttggc tccaggaccc ctccctagtt atgctgcaga cactgccggc | 1200 |
| tcccagctcc atgctgtgcc tgtgctccgc gtctctcatg cagaggagga aggtgaggac | 1260 |
| agctgaaccc gtggggcagc tatggtgtgg gccgagacac gcacatgggt gtccatgaat | 1320 |
| gcagggcaca cgccaagcac gtagggtctg catgcagggc acacgcatgg gcactgtgtg | 1380 |
| cacacagtgg aaatcagtgc tgcccaccctt gccccgggc cagcagccac tgctcccagc | 1440 |
| acaccctgcc ctacctgcag agcgggtacc ccctgaggat gatgagtact ctgaatactc | 1500 |
| cgagtattct gtggaggagt accaggaccc tgaagctcct tgggatagtg atggtgagaa | 1560 |
| tgggggggctg cgcccagcgg ggtctgggga ggggcaggca gggctgagcc ctgctgacct | 1620 |
| ccccctgacc tttcaaccct ctctgattcc cacaaaccct gctgacttga ccccattggc | 1680 |
| ccagacccct gttccctgcc actggatgag ggctcctgca ctgcctacac cctgcgctgg | 1740 |
| taccatcggg ctgtgacagg cagcacagag gcctgtcacc cttttgtcta tggtggctgt | 1800 |
| ggagggaatg ccaaccgttt tgggacccgt gaggcctgcg agcgccgctg cccacccgg | 1860 |
| gtggtccaga gccagggac aggtatgggc tgagccccca ccgtgggaa ctgggcactg | 1920 |
| agcctgcctg gatcgggttc tgggggagga gtccttgggc cagggttcca ggtcagggtc | 1980 |
| ctggaggaga cgctccctcg cagtagggga cctggggcag acgcccagac caaagagctg | 2040 |
| aatatagagc cccagccgtg gagccccag tagggtcccc ttccatgttc cctccttttaa | 2100 |
| agacctaagt atggacccct ctgaggtcag agccccact tcctgttgta gcctccgctc | 2160 |
| cctccccttg gcggtgcctc tgcctgagcg tctccgggga aggtcagatg gctgacgacc | 2220 |
| gtttccaacc tgtcctcacc aggtactgcc caggactgag gcccagataa tgagctgaga | 2280 |
| ttcagcatcc cctggaggag tcgggtctc agcagaaccc cactgtccct ccccttggtg | 2340 |
| ctagaggctt gtgtgcacgt gagcgtgcgt gtgcacgtcc gttatttcag tgacttggtc | 2400 |
| ccgtgggtct agccttcccc cctgtggaca aacccccatt gtggctcctg ccaccctggc | 2460 |
| agatgactca ctgtgggggg gtggctgtgg gcagtgagcg gatgtgactg gcgtctgacc | 2520 |
| cgcccctga cccaagcctg tgatgacatg gtgctgattc tggggggcat taaagctgct | 2580 |
| gttttaaaag gctcctgttg tgactgtttg gaagatggg gggtttcaag ggggaaggtt | 2640 |
| ttccttgggg ggttggtatt attctgcatg ggtacagagt ccctctgccc agtcctggtc | 2700 |
| actgtcttgt gattctcagt ccccaacttg tccccggaaa agagtagata gggtgggggc | 2760 |
| taaggacacc cccggagggg atgagtcata gtgggggc tgcctcatgc caggaagcat | 2820 |
| gtaccagctc ccaccccagg gggctgaggg agataaatgg gccctgaagc ggggtagagg | 2880 |

```
gtcagaccac aggacagtag tgcctggccc cagccccagg cagccacagc aggctgcctt    2940
accccagaag cagctggtgg cggtaggact gggttgggtc gggatgggaa gggtcttgga    3000
ggttgagtgg atgtggggtt tggctttatg gagggcttgg acccagggga ctctgggatc    3060
tctggctgct tttctgcctc tgagatccga ttcctgccct tctgtttcct ggatcagctg    3120
caagctctcc tgctgagaac cgcctgccct cctgtggact ctgtgtttct gtctgaatct    3180
ttctttccat catgctgtct gtctctggga tggtttctgt ctgtctttt  cttctagtct    3240 ccattttgct ctgcctccat ctccttcatc tccctctctt gctgtccctc tgtctctgga    3300
tttctttgtt tctttttttc tgtcttgctt tctgcctctt tgtctcattc tggctctcct    3360
cttgtctccc cttctctgtc tctggcctgg cctggcctct ctaacccctt tctcggtgtc    3420
ttcctctctc tccatccccc gctctgtcac tctgcccttg ccatctgtct ctgtccatgg    3480
accccagttg accagagccc ctgccctgag cccattttct ccttgcagcc                3530
```

PROMOTER SEQUENCES FOR UROCORTIN II AND THE USE THEREOF

CROSS-REFERENCE TO RELATED APPLICATION

This application claims the benefit of provisional application Ser. No. 60/381,121, filed on May 16, 2002, and provisional application Ser. No. 60/423,642, filed on Nov. 1, 2002, both of which are herein incorporated by reference.

STATEMENT REGARDING FEDERALLY SPONSORED RESEARCH OR DEVELOPMENT

This invention was made with United States government support awarded by the following agency: NIH MH40855. The United States has certain rights in this invention.

BACKGROUND OF THE INVENTION

In modern society stress and its consequences are prevalent and result in considerable distress and alterations in physical health and social and occupational functioning. At its extreme, stress can lead to disabling neuropsychiatric problems which include depression, anxiety disorders, post-traumatic stress disorder and other illnesses (Mitchell, 1998; Arborelius et al., 1999). Recent studies demonstrate the potent effects of stress on the body and brain. For example, chronic and intense stress can result in alterations in the region of the brain that plays an important role in memory (McGaugh and Roozendaal, 2002). In addition, stress can negatively impact cardiovascular function, immune function and gastrointestinal physiology (Tache et al., 2001; Beglinger and Degen, 2002; Coste et al., 2002; Gasparotto et al., 2002; Vanitallie, 2002).

It is estimated that 10% of the population suffers from depression and another 15% from clinically significant anxiety. This high incidence of stress-related problems is reflected by the fact that approximately 50% of visits to primary care doctors are stress and/or psychologically related.

Current treatments for stress and its disorders are highly sought after and include the traditional anti-anxiety drugs like Valium and Xanax. More recently newer antidepressants like Prozac have been used to treat depression, anxiety and other stress related problems. It is estimated that $13 billion was spent last year in the U.S. on drugs like Prozac and Paxil. However, these treatments still suffer from lack of efficacy in approximately 30% of the individuals treated. Among those who do respond, only about 50% of them will return to normal function. In addition, these treatments have bothersome side-effects (50% have marked sexual dysfunction) which make treatment with these drugs unacceptable for many individuals. Since depression and anxiety are recurrent and chronic disorders it is important that patients are comfortable taking their medication over a long period of time. Overactivity of the corticotropin-releasing factor (CRF) system is implicated in depression and anxiety and treatments aimed at this system may be very effective (Reul and Holsboer, 2002).

Studies in animals demonstrate that antagonism of the CRF system blocks the distress and physical effects related to stress (Takahashi et al., 2001; Bakshi et al., 2002). Studies in humans show that the CRF system in the brain is overactive in patients with depression, anxiety disorders and other neuropsychiatric problems (Nemeroff, 1989; Chappell et al., 1996; Fossey et al., 1996; Bremner et al., 1997; Mitchell, 1998; Baker et al., 1999). In addition, human and animal studies demonstrate that many effective antidepressant treatments decrease brain CRF activity (Veith et al., 1993). Based on these findings the pharmaceutical industry is currently intensively searching for orally administered compounds that will block or reduce the effects of CRF in the brain. Already some compounds have been identified and are in the early stages of human studies (Zobel et al., 2000).

The CRF system is now known to consist of at least seven components. CRF is a neurotransmitter that is released from neurons and has its effects by interacting with CRF receptors located on adjacent brain cells. Urocortin (UCN), urocortin II (UCN II) and urocortin III (UCN III) are other neurotransmitters similar to CRF that also interact with the system (Vaughan et al., 1995; Lewis et al., 2001; Reyes et al., 2001). Once stimulated the receptors activate intracellular processes which mediate the stress effects.

CRF produces its effects by interacting with two different receptors termed CRF1 and CRF2 (Chen et al., 1993; Penin et al., 1995). Multiple isoforms of the two receptors exist. For example, there are three different isoforms of the CRF2 receptor, termed "CRF2α," "CRF2β" and "CRF2γ" (Lovenberg et al., 1995; Kostich et al., 1998). In addition to CRF1 and CRF2 receptors, there also exists a protein that is found in brain cells that functions to inactivate CRF after it is released termed "CRF binding protein" (Potter et al., 1991).

While much is known about the biology of CRF, considerably less is understood about the urocortin family of peptides. To date three different urocortin peptides have been identified: UCN, UCN II and UCN III. These peptides are likely to be important in mediating stress-induced behavior because it has been found that CRF knockout mice exhibit normal stress-induced behavioral responses that are blocked by CRF receptor antagonism (Weninger et al., 1999). UCN is found in several brain regions that contain R2α (Kozicz et al., 1998; Bittencourt et al., 1999). UCN II and UCN III are highly selective for R2α (Lewis et al., 2001; Reyes et al., 2001). UCN II mRNA is found in the supraoptic and arcuate hypothalamic nuclei and in the locus coeruleus, rostral pons, and motor nuclei. UCN III is found in the hypothalamus, amygdala, and brainstem of rats, and is the rodent analog of the newly discovered human peptide, stresscopin (Hsu and Hsueh, 2001).

SUMMARY OF THE INVENTION

In one aspect, the present invention relates to an isolated nucleic acid containing a human UCN II promoter sequence selected from the 3527 bp upstream of the transcription start site (nucleotides 1 to 3527 of SEQ ID NO:1), the 3030 bp upstream of the transcription start site (nucleotides 498 to 3527 of SEQ ID NO:1), the 2451 bp upstream of the transcription start site (nucleotides 1077 to 3527 of SEQ ID NO:1), the 1987 bp upstream of the transcription start site (nucleotides 1541 to 3527 of SEQ ID NO:1), the 1426 bp upstream of the transcription start site (nucleotides 2102 to 3527 of SEQ ID NO:1), the 931 bp upstream of the transcription start site (nucleotides 2597 to 3527 of SEQ ID NO:1), the 533 bp upstream of the transcription start site (nucleotides 2995 to 3527 of SEQ ID NO:1), the 380 bp upstream of the transcription start site (nucleotides 3148 to 3527 of SEQ ID NO:1), or the 195 bp upstream of the transcription start site (nucleotides 3333 to 3527 of SEQ ID NO:1). Some of these sequences contain at least one cAMP regulatory element (CRE), one glucocorticoid regulatory element (GRE) site or both. Further, the promoter activity of at least some of the sequences can be modulated by CRF.

In another aspect, the present invention relates to a nucleic acid that contains a human UCN II promoter sequence as described above and a heterologous reporter gene operably linked to the sequence. The nucleic acid can be an expression vector and can be provided in a host cell.

Other aspects of the invention relate to methods of screening for agents that may alter the activity of human UCN II promoter, methods of determining whether a fragment of the human UCN II promoter can drive transcription under specific conditions, methods of determining which region of the human UCN II promoter interacts with an agent that is known to alter the activity of the promoter, methods of screening for agents that can alter the activity of human UCN II promoter through CRE or GRE, and methods of screening for agents that can affect the modulation of the human UCN II promoter activity by cAMP level, glucocorticoid receptor activity or CRF receptor activity.

An agent identified by the method of the present invention may be used to treat various psychopathologies described above, including depression, generalized anxiety, social anxiety, post traumatic stress and panic disorder. Additionally, an agent identified may also be useful in the treatment of other illnesses associated with stress such as irritable bowel syndrome and heart disease.

Besides controlling how much UCN II is expressed, the promoter region of the human UCN II gene is also responsible for determining where in the body and when during development UCN II is expressed. Thus, fragments of the human UCN II gene promoter region disclosed herein can be used to identify those elements that are important for tissue and development stage specific expression by conducting experiments in cells from specific tissues and development stages. Once these elements are identified, agents that can alter tissue and development stage specific expression can be identified. These agents may be advantageous in treating stress-related problems over prior art treatment strategies because the agents target UCN II expression in specific regions that are most important in an illness. Thus side effects seen in prior art receptor antagonists treatment due to indiscriminate inhibition of the receptor activity throughout the brain and body can be avoided. For example, the locus coeruleus is located deep in the brain and is thought to be pivotal in mediating the effects of CRF and related peptides in depression and anxiety. Drugs that specifically target UCN II in the locus coeruleus will leave other sites (cortex, brain stem, heart, and hypothalamus) unaffected.

In yet another aspect, the present invention relates to a method of modulating the activity of a human UCN II promoter sequence that contains at least one CRE, GRE or both. The method involves modulating the CRE or GRE activity.

In still another aspect, the present invention relates to a method of modulating UCN II expression in a cell. The method involves modulating cellular CRF receptor activity.

BRIEF DESCRIPTION OF THE SEVERAL VIEWS OF THE DRAWINGS

FIG. 1 shows the UCN II promoter region. The arrow identifies the putative transcription start site which corresponds to position +1. The numbering in the right hand margin is relative to this putative transcription start site. Underlined sequence correspond to the location of the core consensus sequence of putative cis-regulatory elements. TGAC represents a coding strand CRE. GTCA represents a non-coding strand CRE. TGTC represents a coding strand GRE.

DETAILED DESCRIPTION OF THE INVENTION

Figure 2:
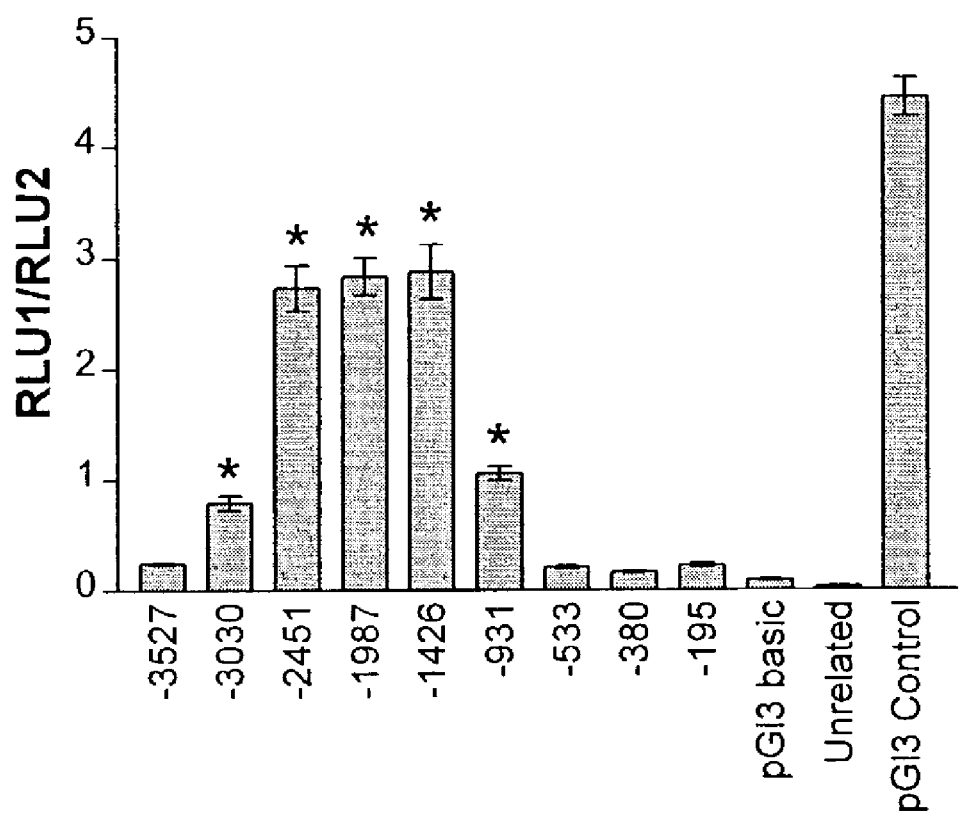
FIG. 2 shows basal levels of expression from UCN II promoter fragments in CHO-K1 cultures (*$P<0.001$).

The term "isolated nucleic acid" used herein means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of clones, e.g., as these occur in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine.

We have cloned the promoter region of the human UCN II gene. Various fragments of the promoter region have been generated and tested for promoter activity in two cell lines. When the P value is set to be less than 0.001, all fragments tested, with the exception of the −3527 fragment, had promoter activity above the background level in at least one of the cell lines with some fragments having much higher activities than others. Sequences and activities of various sequences are shown in the Example below. Further, five CRE and one GRE sites have been identified in the promoter region of the human UCN II gene. We have demonstrated that at least three of the CRE sites and the GRE site are active under the conditions described in the Example in that the promoter activity can be regulated through these sites. In addition, we have also shown that the promoter activity of the human UCN II gene can be regulated by CRF.

In one aspect, the present invention relates to an isolated nucleic acid containing a human UCN II promoter sequence selected from the 3527 bp upstream of the transcription start site (nucleotides 1 to 3527 of SEQ ID NO:1), the 3030 bp upstream of the transcription start site (nucleotides 498 to 3527 of SEQ ID NO:1), the 2451 bp upstream of the transcription start site (nucleotides 1077 to 3527 of SEQ ID NO:1), the 1987 bp upstream of the transcription start site (nucleotides 1541 to 3527 of SEQ ID NO:1), the 1426 bp upstream of the transcription start site (nucleotides 2102 to 3527 of SEQ ID NO:1), the 931 bp upstream of the transcription start site (nucleotides 2597 to 3527 of SEQ ID NO:1), the 533 bp upstream of the transcription start site (nucleotides 2995 to 3527 of SEQ ID NO:1), the 380 bp upstream of the transcription start site (nucleotides 3148 to 3527 of SEQ ID NO:1), or the 195 bp upstream of the transcription start site (nucleotides 3333 to 3527 of SEQ ID NO:1).

In another aspect, the present invention relates to a nucleic acid, which can but does not have to be an expression vector, that contains a human UCN II promoter sequence as described above and a heterologous reporter gene operably linked to the sequence. Such a nucleic acid is useful in many of the methods described below, which involve the determination of the promoter activity of a promoter sequence. The term "reporter gene" is defined here to encompass any polynucleotide the transcription of which under the control of a promoter sequence, the subsequent translation thereof, or both can be readily detected by a skilled artisan. Thus, the reporter gene does not have to encode a full length protein. In some instances, the reporter gene can even be an oligonucleotide. In one embodiment, the reporter gene is a polynucleotide that encodes a protein with a detectable activity.

In another aspect, the present invention relates to a cultured cell that contains a nucleic acid described above. In one embodiment, the cell is a primarily cultured cell such as a primarily cultured central nervous system cell. In another embodiment, the cell is a cell of an immortalized cell line.

In another aspect, the present invention relates to a method for screening for an agent that may alter the human UCN II promoter activity. The method first involves providing a nucleic acid that contains a human UCN II promoter sequence described above that is operably linked to a reporter gene. The nucleic acid is next exposed to conditions suitable for the promoter sequence to drive the transcription of the reporter gene to induce its expression. Two groups of nucleic acids can be set up here. In one group, the expression of the reporter gene is being induced in the presence of a test agent. In the other group (control group), the expression is being induced in the absence of the test agent. The expression of the reporter gene in both groups can then be measured and compared. A higher or lower expression in the test agent group than in the control group indicates that the agent may alter human UCN II promoter activity.

A skilled artisan is familiar with the assay systems that can be used for measuring the expression of a reporter under the control of a promoter sequence and the present invention is not limited to any particular assay systems. In the Example described below, an expression vector containing a human UCN II promoter sequence and a luciferase reporter gene was introduced into either CHO-K1 or CATH.a cells and the expression of the reporter gene was measured by the luciferase activity. It is understood that other cells and reporter genes can also be used. Furthermore, the expression of the reporter gene can also be measured at the mRNA level or at the protein level with a method other than assaying the enzyme activity. For example, the amount of a reporter gene product can be measured by the use of an antibody specific for the product using an ELISA assay.

As another example, a cell-free transcription assay or transcription-translation assay can be used to measure the expression of a reporter gene. When a transcription assay is used, the expression of the reporter gene can be determined at the mRNA level. When a transcription-translation assay is used, the expression of the reporter gene can be measured at both the mRNA level and the protein or peptide level.

The suitable conditions for different human UCN II promoter sequences to drive transcription may be different. For instance, as shown in the Example below, a particular human UCN II promoter sequence may be able to drive transcription in one cell type but not another. For a particular human UCN II promoter sequence, suitable transcription conditions, if not already known, can be readily determined by a skilled artisan.

In another aspect, the present invention relates to a method for determining whether a fragment of the 3527 bp upstream of the transcription start site of the human UCN II promoter region is functional under a set of conditions of interest (e.g., in a specific cell type). A functional fragment is defined as a fragment that can drive transcription under the set of conditions. The method involves providing a nucleic acid that contains the fragment and a heterologous reporter gene operably linked to the fragment, subjecting the nucleic acid to the set of conditions of interest, measuring the expression level of the reporter gene, and comparing the expression level to a suitable negative control wherein a higher than negative control expression level indicates that the fragment is functional. Suitable negative controls can be readily determined by a skilled artisan. An isolated nucleic acid that contains a functional fragment identified, a nucleic acid that contains the functional fragment operably linked to a heterologous reporter gene, and a host cell that contains the nucleic acid with the functional fragment and the reporter gene are also within the scope of the present invention. Also within the scope of the present invention is a method of using the functional fragment identified to screen for agents that may alter the activity of human UCN II promoter as described above.

In another aspect, the present invention relates to a method of determining which region of the human UCN II promoter interacts with an agent known to alter the activity of the promoter. The method first involves providing multiple groups of nucleic acids in which a reporter gene is operably linked to a fragment of the −3527 bp upstream of the transcription start site of the human UCN II promoter and wherein the nucleic acids of the same group contain the same fragment and the nucleic acids in different groups contain different fragments. The nucleic acids are next subject to conditions suitable for the fragments to drive the transcription of the reporter gene. The expression of the reporter gene in the absence and presence of the agent is then measured and compared, and the effects of the agent on the promoter activity of different fragments are determined. Finally, the effects of the agent on the promoter activity of different fragments are compared and the region of the human UCN II promoter that interacts with agent can be identified.

In another aspect, the present invention relates to a method for screening for an agent that can alter the activity of human UCN II promoter through a CRE or GRE site, or a method for determining whether an agent that is known to alter the human UCN II promoter activity alters the activity through a CRE or GRE site. The method involves providing a first human UCN II promoter sequence that contains at least one CRE or GRE site, providing a second human UCN II promoter sequence that is the same as the first sequence except that the CRE or GRE site is mutated, and determining and comparing the effect of the agent on the promoter activity of the first and second sequences wherein a difference in effect indicates that the agent can alter the human UCN II promoter activity through a CRE or GRE site. The effect of the agent on the promoter activity of the first and second sequences can be determined as described above by employing nucleic acids that contain the first or the second sequence and a reporter gene. Although substitution mutations of CRE and GRE sites were employed in the Example below, other mutations such as insertion and deletion mutations can also be used in the method.

Five CRE sites (TGAC) have been identified within the human UCN II promoter region (at −3487, −2400 and −1315 bp relative to the TSP on the coding strand, as well as −3467 and −1402 bp on the non-coding strand). One GRE site (TGTC) has also been identified (at −1297 bp relative to the TSP on the coding strand). Under the specific assay conditions of the Example below and with a P value set at less than 0.001, only the −1426 bp upstream of the transcription start site of the human UCN II gene was shown to be responsive to GRE-related regulation. While the −1426 bp fragment is a suitable human UCN II promoter sequence for the screening method, it is understood that other fragments containing the GRE site, whether shown in the Example below or not, may be useful either with a higher P value or under other conditions (e.g., in other cell lines). A skilled artisan can readily identify and use these fragments. Under the specific conditions in the Example below, all human UCN II promoter sequences tested that contain at least one CRE site were responsive to CRE-related regulation in at least one of the two cell lines used for testing. Thus, all these sequences are suitable sequences for the screening method. It should be noted that under different conditions (e.g., different cell lines), the relative activity of the CRE sites may be different. A skilled artisan can readily determine which CRE site is important under a specific set of conditions. In addition, human UCN II promoter sequences other than those tested in the Example below may also be useful for the method. These sequences can be readily identified and used in the screening method by a skilled artisan.

In another aspect, the present invention relates to a method for screening for an agent that can affect the modulation of the human UCN II promoter activity by cellular cAMP level, cellular glucocorticoid receptor activity or cellular CRF receptor activity. The method involves providing a host cell that contains a human UCN II promoter sequence and a reporter gene operably linked to the promoter sequence wherein the expression of the reporter gene controlled by the promoter sequence can be modulated by cellular cAMP level, cellular glucocorticoid receptor activity or cellular CRF receptor activity, changing the cellular cAMP level, the cellular glucocorticoid receptor activity or the cellular CRF receptor activity, exposing the cell to a test agent, determining the expression level of the reporter gene, and comparing the expression level to that of a control cell that is not exposed to the test agent wherein a higher or lower than control expression indicates that the test agent can affect the modulation of the human UCN II promoter activity by cAMP level, glucocorticoid receptor activity or CRF receptor activity.

Suitable promoter sequences for the method whose activity can be modulated by cellular cAMP level and cellular glucocorticoid receptor activity have been described above as those containing at least one CRE or GRE site. Methods and agents that can be used to change the cellular cAMP level or glucocorticoid receptor activity are known to a skilled artisan. In the Example below, forskolin and IBMX were used to increase the cAMP level and dexamethasone was used to bind to glucocorticoid receptor. Other methods of changing the cellular cAMP level and glucocorticoid receptor activity can also be used.

Under the specific assay conditions of the Example below and with a P value set at less than 0.05, the −1987 upstream and the −1426 bp upstream of the transcription start site of the human UCN II gene were shown to be responsive to CRF-related regulation. While the −1987 and the −1426 bp fragments are suitable sequences for the method, it is understood that other fragments, whether shown in the Example below or not, may be useful either with a higher P value or under other conditions (e.g., in other cell lines). A skilled artisan can readily identify and use those fragments in the method.

In another aspect, the present invention relates to a method for modulating the promoter activity of a human UCN II promoter sequence that contains at least one CRE or GRE site. The method involves modulating the CRE or GRE activity sufficiently to modulate the promoter activity. A skilled artisan is familiar with how the activity of a CRE or GRE site can be modulated. For example, forskolin and IBMX can be used to increase the cellular cAMP level to modulate the activity of a CRE site and dexamethasone can be used to activate a cellular glucocorticoid receptor to modulate the activity of a GRE site.

In another aspect, the present invention relates to a method for modulating UCN II expression in a cell by changing the activity of a CRF receptor sufficiently to modulate the UCN II expression in the cell. A skilled artisan is familiar with how to change the activity of a CRF receptor.

EXAMPLE

Human UCN II Promoter

To identify a publicly available clone that contained the human UCN II gene, we performed a BLAST search of the GenBank database using the human UCN II cDNA sequence (GenBank accession # AF320560; Hsu and Hsueh, 2001).

This search identified clone RP5-1034C16, which contained the entire UCN II gene within its 60,660 bp insert. The PAC clone was then purchased from Research Genetics (Huntsville, Ala.). To obtain the fragment corresponding to the promoter region of the UCN II gene, it was necessary to first subclone into an intermediate vector, pRL-null (Promega, Madison, Wis.) prior to subcloning into the reporter construct that would be used to transfect cells, pGL3-basic (Promega). A 5357 bp fragment of the human UCN II gene corresponding to the promoter region was excised with the restriction enzyme Hinc II. This fragment was subcloned into the vector pRL-null that had been digested with Nar I and blunt ended with T4 DNA polymerase. This insert was then removed from the pRL-null construct with Spe I and Sal I and subcloned into the pGL3-basic vector that had been digested with Nhe I and Xho I. To generate truncated promoter fragments of 3.5 kb and 1.75 kb, we digested the 5357 bp clone with Sac I or Kpn I to remove portions of DNA from the 5' end of the promoter, respectively. To generate an additional series of promoter fragments we used a common reverse (3') primer that ended 3 bp downstream of the putative transcription start point (TSP, nucleotide 3528 of SEQ ID NO:1), we generated sequentially smaller fragments of the UCN II promoter region through PCR with several forward (5') primers. The constructs generated were from −3527, −3030, −2451, −1987, −1426, −931, −533, −380, and −195 bp and relative to the TSP through +3 bp (referred to as the −3527, −3030, −2451, −1987, −1426, −931, −533, −380, and −195 bp constructs, respectively, See Sequence Listing section for location of TSP). Human genomic DNA (Clontech, Palo Alto, Calif.) was used as template for the PCRs. These PCR products were subcloned using T/A cloning into the vector pCR2.1 (Invitrogen Life Technologies, Carlsbad, Calif.). The inserts were then removed by digestion with Sac I and Xho I and subcloned into pGL3-basic that had been digested with the same two enzymes.

Production of Transfected Cell Lines

The above constructs containing the human UCN II promoter fragments placed upstream of the firefly luciferase gene can be used to transfect immortalized cell lines. The constructs can be transfected into CHO-K1 cell lines using Lipofectamine 2000 (Invitrogen Life Technologies). Primary cultures of the central nervous system, as well as additional immortalized cell lines, are also appropriate for these transfections. To control for transfection efficiency, the cells can also be co-transfected with the pRL-TK vector (Promega). The pRL-TK vector contains the *Renilla* luciferase gene downstream of the herpes simplex virus thymidine kinase promoter, a promoter which provides low to moderate levels of expression. Cell lysates can be assayed for total protein using the BCA assay (Pierce, Rockford, Ill.) to standardize for the protein extraction. The level of reporter gene expression from a standardized amount of cell extract can be quantified by measuring luciferase activity using a luminometer (EG&G Wallac, Gaithersburg, Md.) and the dual-luciferase reporter assay system (Promega). Firefly luciferase activity reflects UCN II promoter activity and *Renilla* luciferase activity can be used to normalize data between experiments.

Characterization of Basal Expression from UCN II Promoter Fragments

Using the methods described above, transient transfections of CHO-K1 cultures were assayed for reporter gene expression (See FIG. 2). In these experiments, three basic controls were utilized. The cultures referred to as pGL-3 basic were transfected with a pGL-3 firefly luciferase reporter construct that did not contain an experimental promoter, and with the pRL-TK *renilla* luciferase vector. These cultures should demonstrate a very low level of expression (background levels) and are considered a negative control. The cultures referred to as pGL-3 control were transfected with a construct containing the firefly luciferase reporter downstream of the SV40 viral promoter as well as the pRL-TK *renilla* luciferase vector. These cultures should demonstrate a very high level of expression and are considered a positive control. Finally, the cultures referred to as unrelated were transfected with a construct containing 1916 bp of DNA sequence upstream of the firefly reporter gene and with the pRL-TK *renilla* luciferase vector. The 1916 bp of this construct were a random DNA sequence. These cultures were intended to demonstrate the specificity of our promoter constructs.

Analysis of the data by one-way ANOVA indicates a highly significant finding ($P<0.0001$; $F=138.6$, $R^2=0.9055$). Post-Hoc analysis (Newman-Keuls multiple comparison test) indicates that the −3030, −2451, −1987, −1426, and −931 UCN II promoter fragments exhibited significantly increased expression compared with the pG13 basic construct ($P<0.001$), whereas, the remaining UCN II fragments were not significantly different from pG13 basic. Our results indicate that the −1426 construct had the highest level of expression of the UCN II promoter constructs (See FIG. 2). Our results demonstrate a unimodal pattern of expression in which the −2451, −1987 and −1426 constructs were not significantly different from each other and correspond to a plateau of expression. Our lowest level of expression (−380 construct) was 75% greater than housekeeping levels of expression (pGL-3 basic), and it was 3.7% of the strong expression elicited by the viral promoter (pGL-3 control). Our highest level of expression (−1426 construct) was 2981% greater than housekeeping levels of expression (pGL-3 basic), and it was 65% of the strong expression from the SV40 promoter (pGL-3 control). Furthermore, the scrambled DNA sequence was not able to drive expression above background. Thus, the UCN II promoter constructs function and will be appropriate tools to monitor UCN II specific transcription.

Figure 3:
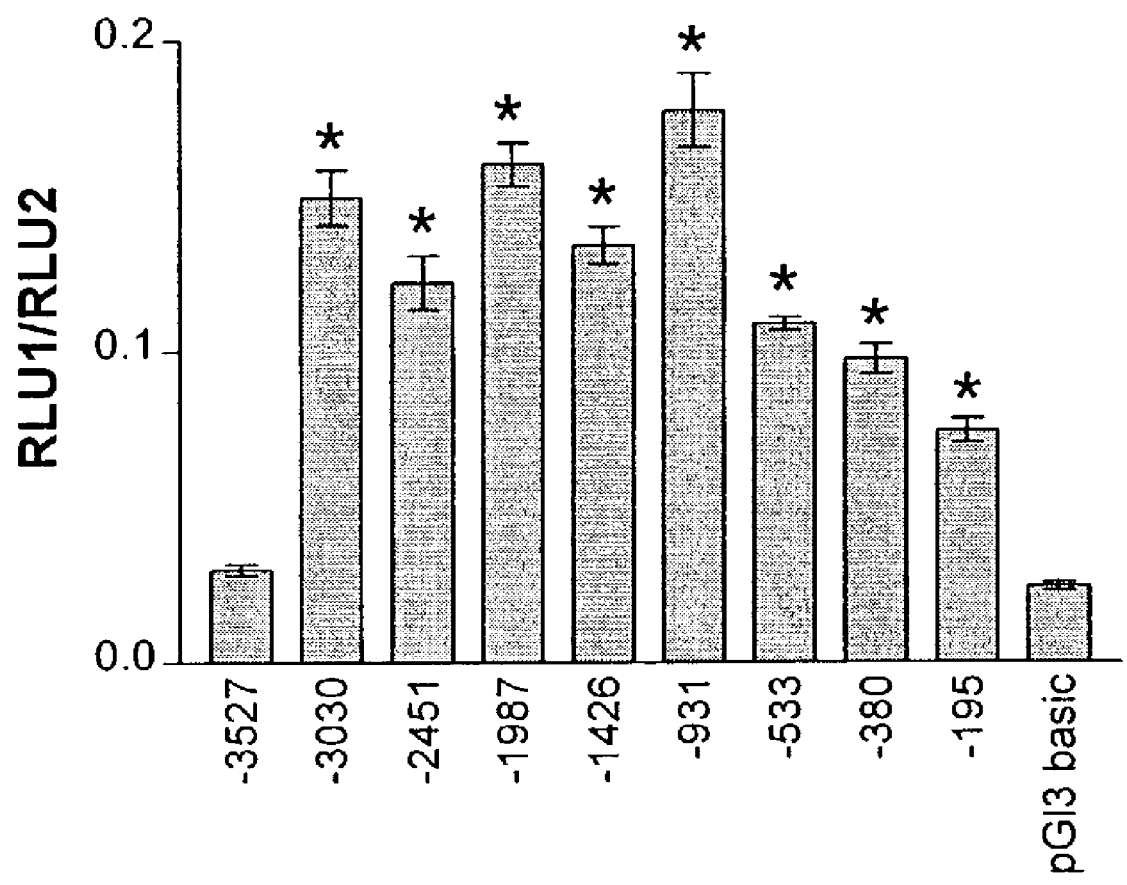
FIG. 3 shows basal levels of expression from UCN II promoter fragments in CATH.a cultures (*$P<0.001$).

It is expected that different cell lines transfected with the UCN II promoter constructs will demonstrate different patterns of expression. This is due to the fact that different cell types will express variable levels of transcription factors, a different complement of transcription factors and/or a particular cell type may express transcription factors unique to this cell type. By examining expression patterns within multiple cell lines, one may be able to identify regions of the UCN II promoter that are important for expression within a particular cell type. This knowledge may allow one to fine tune therapeutic agents that interact with the UCN II promoter so that there is a tissue specific alteration in UCN II expression. This ability may allow the development of pharmaceuticals to treat stress-related disorders that have fewer side effects than currently available treatments. With this goal in mind, CATH.a cultures were transiently transfected with the UCN II promoter constructs and basal levels of expression from these constructs were determined as described above (See FIG. 3). The CATH.a cell line was derived from tissue taken from the mouse locus coeruleus, a region known to express UCN II.

Analysis of the data by one-way ANOVA indicates a highly significant finding ($P<0.0001$; $F=82.97$, $R^2=0.9577$). Post-Hoc analysis (Newman-Keuls multiple comparison test) indicates that the −3030, −2451, −1987, −1426, −931, −533, −380 and −195 UCN II promoter fragments exhibited significantly increased expression compared with the pG13 basic construct (P<0.001), whereas, the −3527 UCN II fragment was not significantly different from pG13 basic. Our results indicate that the −931 construct had the highest level of expression of the UCN II promoter constructs (See FIG. 3), whereas, the −3527 construct had the lowest. Our results demonstrate a diffuse unimodal pattern of expression with no clear plateau of expression. Our lowest level of expression (−3527 construct) was 22% greater than housekeeping levels of expression (pGL-3 basic). Our highest level of expression (−931 construct) was 617% greater than housekeeping levels of expression (pGL-3 basic). Expression from the UCN II promoter was lower in CATH.a cultures compared to CHO-K1 cultures. Without intending to be limited by theory, the higher level of expression within a cell line (CHO-K1) is likely due to ubiquitous gene expression that may occur in CHO-K1 cells compared to the more tightly controlled gene expression that may occur in CATH.a cells. However, a greater number of UCN II promoter fragments showed statistically significant expression with the CATH.a cultures compared to the CHO-K1 cultures. These findings emphasize the utility of examining UCN II expression within multiple cell lines.

Figure 4:
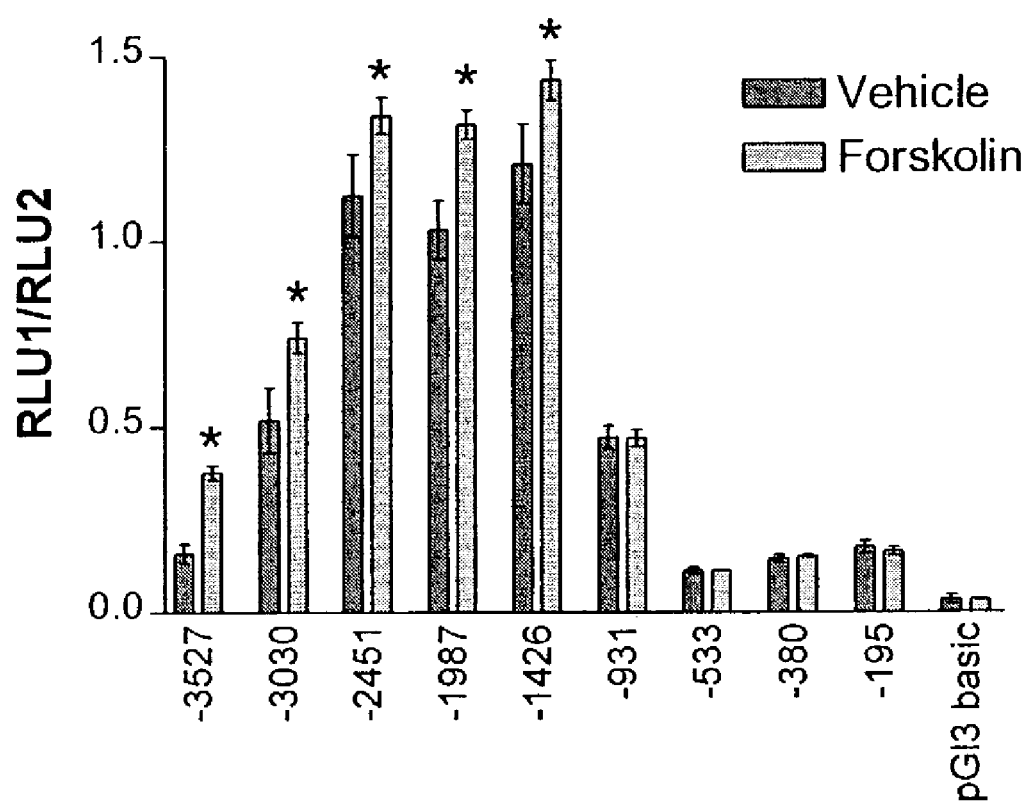
FIG. 4 shows forskolin and IBMX-induced expression from UCN II promoter fragments in CHO-K1 cultures (*$P<0.001$).

Characterization of Forskolin and IBMX-Induced Expression from UCN II Promoter Fragments Using the methods described previously, CHO-K1 cultures were transiently transfected with the UCN II promoter constructs. Immediately following transfection equal numbers of cultures (N=12 per group) were treated with either 10 µM forskolin and 0.25 mM 3-isobutyl-1-methylxanthine (IBMX) or were given vehicle. Twenty-two hours following treatment, the cultures were harvested and assayed for luciferase activity (see FIG. 4). Forskolin activates adenylate cyclase which increases intracellular cAMP levels. IBMX is an inhibitor of cAMP phosphodiesterases, the enzymes which break down cAMP. Increases in cAMP levels would result in the protein kinase A-dependent phosphorylation (activation) of cAMP response element binding protein (CREB). CREB is a well characterized transcription factor known to bind the cAMP response element (CRE), a cis-regulatory element found in the promoter region of many genes. Analysis of the human UCN II promoter sequence (described below in the sequence listing and FIG. 1) with the computer program MatInspector v2.2 using the TRANSFAC 4.0 database of transcription factors showed five putative CRE sites within the human UCN II promoter. The 5' end of the consensus core sequence for the CRE sites (TGAC) was found at −3487, −2400 and −1315 bp relative to the TSP on the coding strand, as well as −3467 and −1402 bp on the non-coding strand of the UCN II DNA. We hypothesized that forskolin and IBMX treatment will alter expression of the UCN II promoter via the CRE sites.

Analysis of the data by two-way ANOVA indicates a highly significant main effect for treatment and construct as well as an interaction (P<0.0001 for all cases). Post-Hoc analysis (Bonferroni posttests) indicates that forskolin and IBMX treatment significantly increased expression within the −3527, −3030, −2451, −1987 and −1426 constructs (P<0.001 for all cases) but had no effect on the remaining constructs. Our largest increase was seen with the −3527 construct in which the expression from the forskolin and IBMX-treated cultures was 138% greater than the cultures given the vehicle. The smallest significant increase was seen with the −2451 construct in which forskolin and IBMX increased expression 19% above cultures given the vehicle.

Given the location of the putative CRE regulatory sites, our results demonstrate that some of these sites actively participate in the regulation of UCN II expression. Not a single construct that does not contain a CRE cis-regulatory element was affected by forskolin and IBMX treatment. Every construct that contained a putative CRE element showed an increase in expression when treated with forskolin and IBMX. Furthermore, the −3527 construct, which contains all five putative CRE elements, demonstrated the largest increase in expression following forskolin and IBMX treatment.

Figure 5:
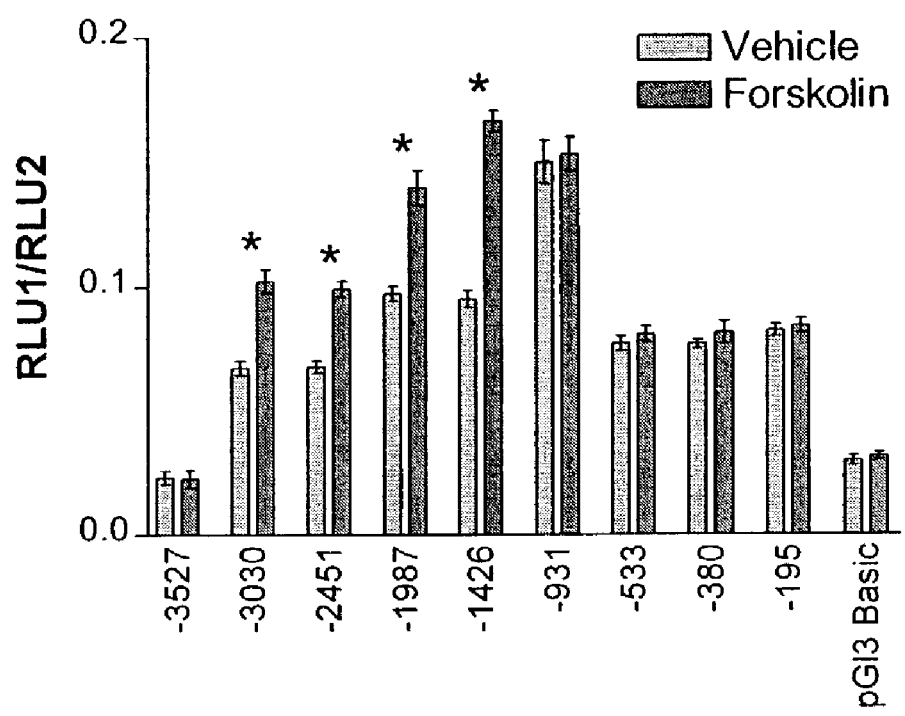
FIG. 5 shows forskolin and IBMX-induced expression from UCN II promoter fragments in CATH.a cultures (*$P<0.001$).

In the following experiments, we confirmed the forskolin and IBMX treatment results in the CATH.a cell line. Using the methods described previously, CATH.a cultures were transiently transfected with the UCN II promoter constructs. Immediately following transfection equal numbers of cultures (N=12 per group) were treated with either 10 µM forskolin and 0.25 mM IBMX or were given vehicle. Twenty-two hours following treatment, the cultures were harvested and assayed for luciferase activity (see FIG. 5).

Analysis of the data by two-way ANOVA indicates a highly significant main effect for treatment and construct as well as an interaction (P<0.0001 for all cases). Post-Hoc analysis (Bonferroni posttests) indicates that forskolin and IBMX treatment significantly increased expression within the −3030, −2451, −1987 and −1426 constructs (P<0.001 for all cases) but had no effect on the remaining constructs. Our largest increase was seen with the −1426 construct in which expression from the forskolin and IBMX-treated cultures was 75% greater than the cultures given the vehicle. The smallest significant increase was seen with the −1987 construct in which expression from the forskolin and IBMX-treated cultures was 44% greater than the cultures given the vehicle. Similar to the results in the CHO-K1 cell line, not a single construct that does not contain a CRE cis-regulatory element was affected by forskolin and IBMX treatment. With the exception of the −3527 construct, every construct that contained a putative CRE element showed an increase in expression when treated with forskolin and IBMX.

Figure 6:
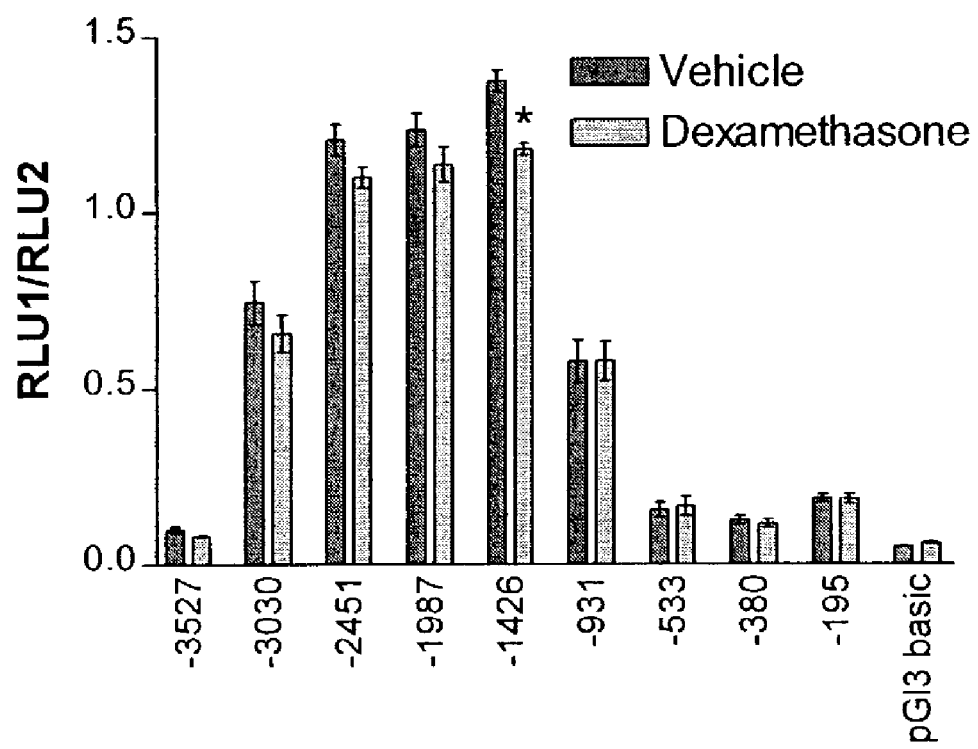
FIG. 6 shows dexamethasone induced expression from UCN II promoter fragments in CHO-K1 cultures (*$P<0.001$).

Characterization of Dexamethasone Induced Expression from UCN II Promoter Fragments Using the methods described previously, CHO-K1 cultures were transiently transfected with the UCN II promoter constructs. Immediately following transfection equal numbers of cultures (N=12 per group) were treated with either 20 µM dexamethasone or with vehicle. Twenty-two hours following treatment, the cultures were harvested and assayed for luciferase activity (see FIG. 6). Dexamethasone is a synthetic glucocorticoid that will bind glucocorticoid receptors located within the cell. Once bound, the receptors will translocate to the nucleus and bind glucocorticoid response elements (GRE) located within the promoter region of many genes. Analysis of the human UCN II promoter sequence (described below in the sequence listing and FIG. 1) with the computer program MatInspector v2.2 using the TRANSFAC 4.0 database of transcription factors showed a single putative GRE site within the human UCN II promoter. The 5' end of the consensus core sequence for the GRE site (TGTC) was found at −1297 bp relative to the TSP on the coding strand of the DNA. We hypothesized that dexamethasone treatment will alter expression of the UCN II promoter via the GRE site.

Analysis of the data by two-way ANOVA indicates a highly significant main effect for treatment and construct as well as an interaction (P<0.0001 for all cases). Post-Hoc analysis (Bonferroni posttests) indicates that dexamethasone treatment significantly decreased expression within the −1426 construct (P<0.001) but had no significant effect on the remaining constructs. This finding represents a 15% decrease compared to the vehicle treated cultures. Given the location of the putative GRE regulatory site, our results demonstrate that this GRE site plays a role in regulating expression of the UCN II gene. Although many of the constructs larger than the −1426 construct showed a trend to decrease expression following dexamethasone treatment, the changes were not significant. Only the −1426 construct, the smallest construct that still contained the putative GRE site, showed a significant decrease in expression. The −931 and smaller constructs were not influenced by dexamethasone.

Figure 7:
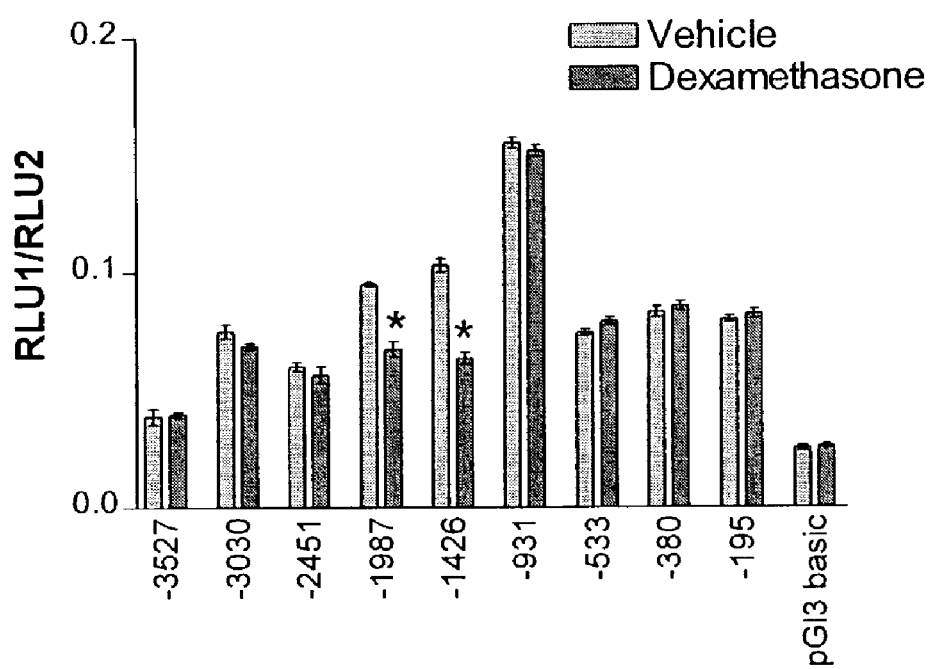
FIG. 7 shows dexamethasone induced expression from UCN II promoter fragments in CATH.a cultures (*$P<0.001$).

In the following experiments, we confirmed the dexamethasone treatment results in the CATH.a cell line. Using the methods described previously, CATH.a cultures were transiently transfected with the UCN II promoter constructs. Immediately following transfection equal numbers of cultures (N=12 per group) were treated with either 20 μM dexamethasone or were given vehicle. Twenty-two hours following treatment, the cultures were harvested and assayed for luciferase activity (see FIG. 7).

Analysis of the data by two-way ANOVA indicates a highly significant main effect for treatment and construct as well as an interaction (P<0.0001 for all cases). Post-Hoc analysis (Bonferroni posttests) indicates that dexamethasone treatment significantly decreased expression within the −1987 and −1426 constructs (P<0.001 for both) but had no effect on the remaining constructs. Our greatest decrease was seen with the −1426 construct in which expression from the dexamethasone-treated cultures was 39% less than the cultures given the vehicle. The smallest significant decrease was seen with the −1987 construct in which expression from the dexamethasone treated cultures was 29% less than the cultures given the vehicle. Similar to the results with the CHO-K1 cell line, the results in the CATH.a cell line demonstrate that the putative GRE site plays a role in regulating the expression of the UCN II gene. Only the two smallest constructs (−1987 and −1426) that contain the GRE site (at −1297) showed a significant effect. The results in the CATH.a cell line differ slightly from the results in CHO-K1 cultures presented above. Both cell lines demonstrated decreases in UCN II expression following dexamethasone treatment. However, the CHO-K1 cultures showed a smaller region of interaction than was identified with the CATH.a cultures.

Characterization of CRF Induced Expression from UCN II Promoter Fragments

Figure 8:
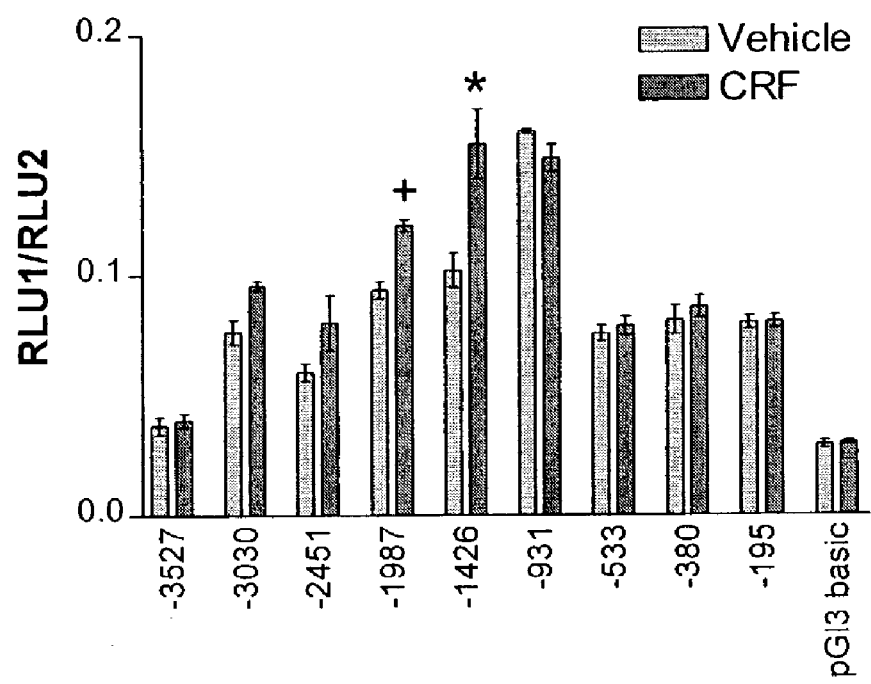
FIG. 8 shows CRF induced expression from UCN II promoter fragments in CATH.a cultures (*$P<0.001$; †$P<0.05$).

Using the methods described previously, CATH.a cultures were transiently transfected with the UCN II promoter constructs. Immediately following transfection equal numbers of cultures (N=4 per group) were treated with either 1 μM CRF or with vehicle. Twenty-two hours following treatment, the cultures were harvested and assayed for luciferase activity (see FIG. 8). CATH.a cultures are known to express CRF receptors and both CRF and UCN II are known ligands for the receptors. Activation of CRF receptors has been shown to stimulate several intracellular pathways that are capable of altering gene expression. The goal of the present experiment was to determine if CRF receptor-dependent second messenger system activation affected UCN II gene expression.

Analysis of the preliminary data by two-way ANOVA indicates a highly significant main effect for treatment and construct as well as an interaction (P<0.0001 for all cases). Post-Hoc analysis (Bonferroni posttests) indicates that CRF treatment significantly increased expression within the −1987 and −1426 constructs (P<0.05 for the −1987 construct and P<0.001 for the −1426 construct) but had no significant effect on the remaining constructs. Our greatest increase was seen with the −1426 construct in which expression from the CRF-treated cultures was 52% greater than the cultures given the vehicle. The smallest significant increase was seen with the −1987 construct in which the expression from the CRF-treated cultures was 29% greater than the cultures given the vehicle. These results demonstrate that activation of CRF receptors can influence expression UCN II.

Characterization of the Functional GRE cis-Regulatory Element

Figure 9:
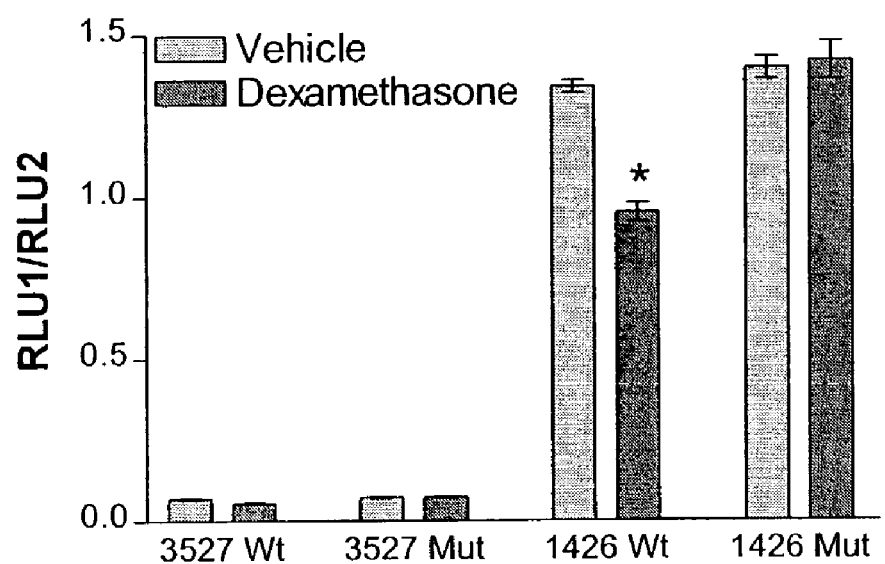
FIG. 9 shows dexamethasone induced expression from wild type and mutated UCN II promoter fragments in CHO-K1 cultures (*$P<0.001$).
Figure 10:
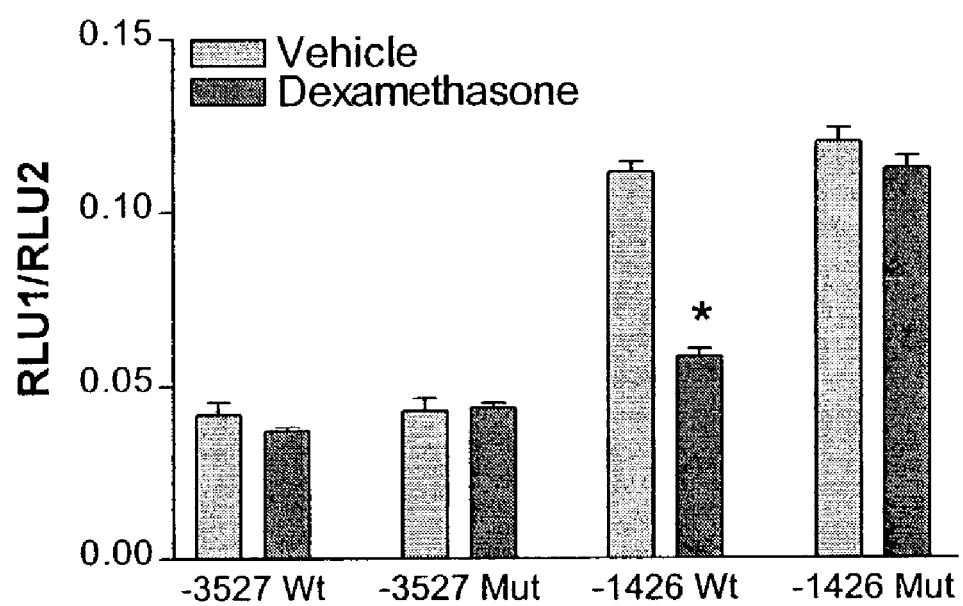
FIG. 10 shows dexamethasone induced expression from wild type and mutated UCN II promoter fragments in CATH.a cultures (*$P<0.001$).

In the experiments described above, we demonstrated that dexamethasone treatment of CHO-K1 or CATH.a cultures transfected with the UCN II constructs elicited a significant decrease in expression from the UCN II promoter. The constructs that demonstrated the significant decrease contained a single putative GRE site (located at −1297). In order to further demonstrate the role of this GRE site in the dexamethasone-induced decrease in expression from the UCN II promoter, site-directed mutagenesis was performed. Using the Quickchange II X1 kit (Stratagene, La Jolla, Calif.) two base pairs of the GRE consensus core sequence were mutated (TGTC→TACC) in both the −3527 and −1426 constructs. CHO-K1 and CATH.a cultures were transfected with both the wild type and mutated −3527 and −1426 constructs. An equal number of cultures (N=12 per group) were treated with either 20 μM dexamethasone or with vehicle. Twenty-two hours following transfection, the cultures were harvested and assayed for luciferase activity (see FIGS. 9 and 10).

The results in the CATH.a cell line are essentially identical to the results with the CHO-K1 cell line. The wild type −3527 construct was unaffected by dexamethasone treatment, as previously shown. Mutation of two base pairs within the consensus core sequence of the GRE site did not significantly affect expression within the −3527 construct when treated with either dexamethasone or vehicle. With the wild type −1426 construct, dexamethasone treatment significantly (P<0.001) decreased expression compared to vehicle treated cultures. Mutation of two base pairs within the consensus core sequence of the GRE site did not significantly affect expression within the −1426 construct when given the vehicle, as compared with −1426 wild type cultures given vehicle. However, mutation of two base pairs within the consensus core sequence of the GRE site had a very dramatic affect on dexamethasone-induced expression. Expression from the mutated −1426 constructs treated with dexamethasone was not significantly different from the mutated −1426 constructs that received vehicle, nor was it significantly different from the wild type −1426 construct that received vehicle. Furthermore, expression from the mutated −1426 construct treated with dexamethasone was significantly greater (P<0.001) than expression from the wild type −1426 construct that received dexamethasone. These results provide further evidence that the GRE site was responsible for the dexamethasone-induced decrease in expression from the UCN II promoter.

Electrophoretic mobility shift assays (EMSA) were performed to further demonstrate that the GRE site is functional. In the EMSA, a radiolabeled oligonucleotide with the native UCN II DNA sequence that contains the GRE site was incubated with nuclear extract from CHO-K1 cultures treated with 20 μM dexamethasone. If the nuclear extract contains a transcription factor capable of binding the oligonuceotide, a protein-DNA complex will form. This protein-DNA complex will migrate more slowly through a bis-acrylamide gel during electrophoresis than the unbound oligonucleotide. The EMSA experiments demonstrated that the wild type GRE oligonucleotide was bound, whereas, an oligonucleotide with a mutated GRE site (same mutation as described above) was not bound. Furthermore, unlabeled wild type oligonucleotide competed away the binding, whereas, unlabeled mutant oligonucleotide or an unlabeled oligonucleotide containing an AP-1 regulatory element did not compete for the binding protein. Therefore, we have demonstrated highly specific binding to the GRE site and that our mutation to the GRE site prevents binding of any transcription factor. Taken as a whole, our results provide convincing evidence that the putative GRE site is functionally important.

Characterization of the Functional CRE cis-Regulatory Elements

Figure 11:
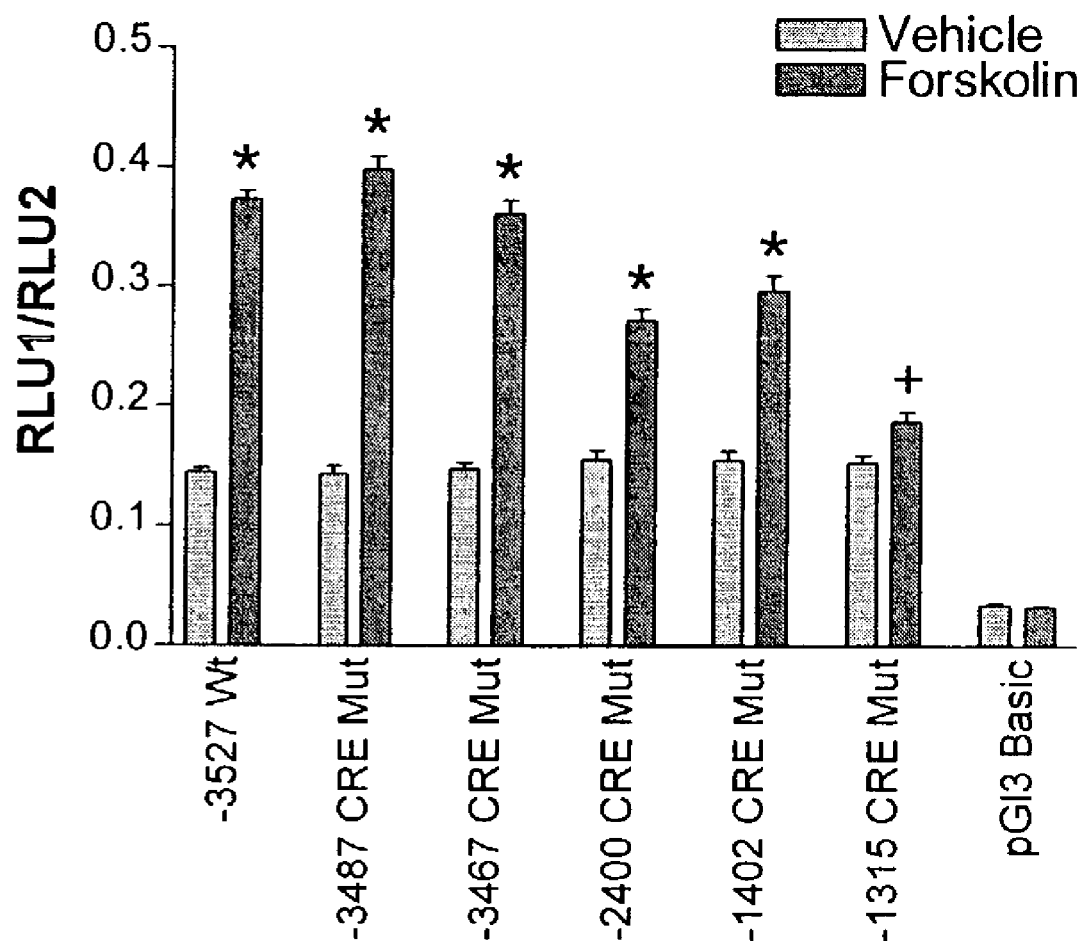
FIG. 11 shows forskolin and IBMX-induced expression from wild type and mutated UCN II promoter fragments in CHO-K1 cultures (*$P<0.001$; †$P<0.05$).

In the experiments described above, we demonstrated that forskolin and IBMX treatment of CHO-K1 or CATH.a cultures transfected with the UCN II constructs elicited a significant increase in expression from the UCN II promoter. The UCN II promoter contains five putative CRE sites (located at −3487, −3467, −2400, −1402, and −1315 bp). Many of the UCN II constructs demonstrated a significant increase in expression following forskolin and IBMX treatment. Furthermore, the UCN II constructs that demonstrated a significant increase in expression all contained more than one CRE site. In order to further demonstrate the relative involvement of a CRE site with the forskolin and IBMX-induced increase in expression from the UCN II promoter, site-directed mutagenesis was performed. Using the Quickchange II X1 kit (Stratagene, La Jolla, Calif.) two base pairs of the CRE consensus core sequence were mutated (TGAC→TTCC) in the −3527 construct. Each CRE site was mutated separately so that five new mutated −3527 constructs were generated, each with a single CRE site mutated. CHO-K1 cultures were transfected with both the wild type and mutated −3527 constructs. An equal number of cultures (N=12 per group) were treated with either 10 µM forskolin and 0.25 mM IBMX or with vehicle. Twenty-two hours following transfection, the cultures were harvested and assayed for luciferase activity (see FIG. 11).

Mutation of two base pairs within the consensus core sequence of any CRE site did not significantly affect expression when given the vehicle, as compared with −3527 wild type cultures given vehicle. Analysis by two-way ANOVA demonstrates that expression from the mutated constructs was significantly increased following forskolin and IBMX treatment, as compared with the respective mutated constructs that received vehicle (P<0.05 for the −1315 construct, P<0.001 for all others). Mutation of either the −3487 or −3467 CRE sites did not significantly affect expression following forskolin and IBMX treatment, when compared to the −3527 wild type cultures treated with forskolin and IBMX. However, expression from the −2400, −1402, and −1315 CRE mutant constructs following forskolin and IBMX treatment was significantly lower than expression from the wild type −3527 construct when given forskolin and IBMX. Without intending to be limited by theory, one interpretation of these results is that the −3487 and −2467 CRE cis-regulatory sites are not involved in the forskolin and IBMX-induced increase in expression from the UCN II promoter in this cell line, whereas, the −2400, −1402 and −1315 CRE sites confer the forskolin and IBMX-induced increases in expression. These results provide further evidence that the CRE sites were responsible for the forskolin and IBMX-induced increase in expression from the UCN II promoter.

Although the invention has been described in connection with specific embodiments, it is understood that the invention is not limited to such specific embodiments but encompasses all such modifications and variations apparent to a skilled artisan that fall within the scope of the appended claims.

REFERENCES

Arborelius L, Owens M J, Plotsky P M, Nemeroff C B (1999) The role of corticotropin-releasing factor in depression and anxiety disorders. J Endocrinol 160:1–12.

Baker D G, West S A, Nicholson W E, Ekhator N N, Kasckow J W, Hill K K, Bruce A B, Orth D N, Geracioti T D, Jr. (1999) Serial CSF corticotropin-releasing hormone levels and adrenocortical activity in combat veterans with posttraumatic stress disorder. Am J Psychiatry 156:585–588.

Bakshi V P, Smith-Roe S, Newman S M, Grigoriadis D E, Kalin N H (2002) Reduction of stress-induced behavior by antagonism of corticotropin-releasing hormone 2 (CRH2) receptors in lateral septum or CRH1 receptors in amygdala. J Neurosci 22:2926–2935.

Beglinger C, Degen L (2002) Role of thyrotrophin releasing hormone and corticotrophin releasing factor in stress related alterations of gastrointestinal motor function. Gut 51 Suppl 1:I45–I49.

Bittencourt J C, Vaughan J, Arias C, Rissman R A, Vale W W, Sawchenko P E (1999) Urocortin expression in rat brain: evidence against a pervasive relationship of urocortin-containing projections with targets bearing type 2 CRF receptors. *J Comp Neurol* 415:285–312.

Bremner J D, Licinio J, Darnell A, Krystal J H, Owens M J, Southwick S M, Nemeroff C B, Charney D S (1997) Elevated CSF corticotropin-releasing factor concentrations in posttraumatic stress disorder. Am J Psychiatry 154:624–629.

Chappell P, Leckman J, Goodman W, Bissette G, Pauls D, Anderson G, Riddle M, Scahill L, McDougle C, Cohen D (1996) Elevated cerebrospinal fluid corticotropin-releasing factor in Tourette's syndrome: comparison to obsessive compulsive disorder and normal controls. Biol Psychiatry 39:776–783.

Chen R, Lewis K A, Perrin M H, Vale W W (1993) Expression cloning of a human corticotropin-releasing-factor receptor. Proc Natl Acad Sci USA 90:8967–8971.

Coste S C, Quintos R F, Stenzel-Poore M P (2002) Corticotropin-releasing hormone-related peptides and receptors. Emergent regulators of cardiovascular adaptations to stress. Trends Cardiovasc Med 12:176–182.

Fossey M D, Lydiard R B, Ballenger J C, Laraia M T, Bissette G, Nemeroff C B (1996) Cerebrospinal fluid corticotropin-releasing factor concentrations in patients with anxiety disorders and normal comparison subjects. Biol Psychiatry 39:703–707.

Gasparotto O C, Ignacio Z M, Lin K, Goncalves S (2002) The effect of different psychological profiles and timings of stress exposure on humoral immune response. Physiol Behav 76:321–326.

Hsu S Y, Hsueh A J (2001) Human stresscopin and stresscopin-related peptide are selective ligands for the type 2 corticotropin-releasing hormone receptor. *Nat Med* 7:605–611.

Kostich W A, Chen A, Sperle K, Largent B L (1998) Molecular identification and analysis of a novel human corticotropin-releasing factor (CRF) receptor: the CRF2gamma receptor. Mol Endocrinol 12:1077–1085.

Kozicz T, Yanaihara H, Arimura A (1998) Distribution of urocortin-like immunoreactivity in the central nervous system of the rat. *J Comp Neurol* 391:1–10.

Lewis K, Li C, Perrin M H, Blount A, Kunitake K, Donaldson C, Vaughan J, Reyes T M, Gulyas J, Fischer W, Bilezikjian L, Rivier J, Sawchenko P E, Vale W W (2001) Identification of urocortin III, an additional member of the corticotropin-releasing factor (CRF) family with high affinity for the CRF2 receptor. Proc Natl Acad Sci USA 98:7570–7575.

Lovenberg T W, Chalmers D T, Liu C, De Souza E B (1995) CRF2 alpha and CRF2 beta receptor mRNAs are differentially distributed between the rat central nervous system and peripheral tissues. Endocrinology 136:4139–4142.

McGaugh J L, Roozendaal B (2002) Role of adrenal stress hormones in forming lasting memories in the brain. Curr Opin Neurobiol 12:205–210.

Mitchell A J (1998) The role of corticotropin releasing factor in depressive illness: a critical review. Neurosci Biobehav Rev 22:635–651.

Nemeroff C B (1989) Clinical Significance of Psychoneuroendocrinology in Psychiatry: Focus on the Thyroid and Adrenal. J Clin Psychiatry 50:13–20.

Perrin M, Donaldson C, Chen R, Blount A, Berggren T, Bilezikjian L, Sawchenko P, Vale W (1995) Identification of a second corticotropin-releasing factor receptor gene and characterization of a cDNA expressed in heart. Proc Natl Acad Sci USA 92:2969–2973.

Potter E, Behan D P, Fischer W H, Linton E A, Lowry P J, Vale W W (1991) Cloning and characterization of the cDNAs for human and rat corticotropin releasing factor-binding proteins. Nature 349:423–425.

Reul J M, Holsboer F (2002) Corticotropin-releasing factor receptors 1 and 2 in anxiety and depression. Curr Opin Pharmacol 2:23–33.

Reyes T M, Lewis K, Perrin M H, Kunitake K S, Vaughan J, Arias C A, Hogenesch J B, Gulyas J, Rivier J, Vale W W, Sawchenko P E (2001) Urocortin II: A member of the corticotropin-releasing factor (CRF) neuropeptide family that is selectively bound by type 2 CRF receptors. Proc Natl Acad Sci USA 98:2843–2848.

Tache Y, Martinez V, Million M, Wang L (2001) Stress and the gastrointestinal tract III. Stress-related alterations of gut motor function: role of brain corticotropin-releasing factor receptors. Am J Physiol Gastrointest Liver Physiol 280:G173–177.

Takahashi L K, Ho S P, Livanov V, Graciani N, Americ S P (2001) Antagonism of CRF(2) receptors produces anxiolytic behavior in animal models of anxiety. Brain Res 902:135–142.

Vanitallie T B (2002) Stress: A risk factor for serious illness. Metabolism 51:40–45.

Vaughan J, Donaldson C, Bittencourt J, Perrin M H, Lewis K, Sutton S, Chan R, Turnbull A V, Lovejoy D, Rivier C, et al. (1995) Urocortin, a mammalian neuropeptide related to fish urotensin I and to corticotropin-releasing factor. Nature 378:287–292.

Veith R C, Lewis N, Langohr J I, Murburg M M, Ashleigh E A, Castillo S, Peskind E R, Pascualy M, Bissette G, Nemeroff C B, Raskind M A (1993) Effect of desipramine on cerebrospinal fluid concentrations of corticotropin-releasing factor in human subjects. Psychiatry Res 46:1–8.

Weninger S C, Dunn A J, Muglia L J, Dikkes P, Miczek K A, Swiergiel A H, Berridge C W, Majzoub J A (1999) Stress-induced behaviors require the corticotropin-releasing hormone (CRH) receptor, but not CRH. *Proc Natl Acad Sci USA* 96:8283–8288.

Zobel A W, Nickel T, Kunzel H E, Ackl N, Sonntag A, Ising M, Holsboer F (2000) Effects of the high-affinity corticotropin-releasing hormone receptor 1 antagonist R121919 in major depression: the first 20 patients treated. J Psychiatr Res 34:171–181.

We claim:

1. A method for screening for an agent that may alter the activity of human urocortin II promoter, the method comprising the steps of:
   (a) providing a nucleic acid that comprises a human urocortin II promoter sequence operably linked to a reporter gene, wherein the promoter sequence is selected from the group consisting of the 3527 bp upstream of the transcription start site (nucleotides 1 to 3527 of SEQ ID NO:1), the 3030 bp upstream of the transcription start site (nucleotides 498 to 3527 of SEQ ID NO:1), the 2451 bp upstream of the transcription start site (nucleotides 1077 to 3527 of SEQ ID NO:1), the 1987 bp upstream of the transcription start site (nucleotides 1541 to 3527 of SEQ ID NO:1), the 1426 bp upstream of the transcription start site (nucleotides 2102 to 3527 of SEQ ID NO:1), the 931 bp upstream of the transcription start site (nucleotides 2597 to 3527 of SEQ ID NO:1), the 533 bp upstream of the transcription start site (nucleotides 2995 to 3527 of SEQ ID NO:1), the 380 bp upstream of the transcription start site (nucleotides 3148 to 3527 of SEQ ID NO:1), and the 195 bp upstream of the transcription start site (nucleotides 3333 to 3527 of SEQ ID NO:1); and
   (b) subjecting the nucleic acid to conditions suitable for the promoter sequence to drive the expression of the reporter gene in the presence of the test agent;
   (c) evaluating the expression of the reporter gene compared to a control nucleic acid that is exposed to the same conditions but without the test agent wherein a higher or lower expression than that of the control nucleic acid indicates that the agent may alter human urocortin II promoter activity.

2. The method of claim 1, wherein the expression is evaluated at the mRNA level.

3. The method of claim 1, wherein the expression is evaluated at the protein level.

4. The method of claim 1, wherein the nucleic acid is provided in a host cell and wherein the host cell is exposed to the test agent in step (b).

5. The method of claim 4, wherein the host cell is a primarily cultured central nervous system cell.

6. The method of claim 4, wherein the host cell is a cell of an immortalized cell line.

7. The method of claim 1, wherein the promoter sequence is the 3527 bp upstream of the transcription start site (nucleotides 1 to 3527 of SEQ ID NO:1).

8. The method of claim 1, wherein the promoter sequence is the 3030 bp upstream of the transcription start site (nucleotides 498 to 3527 of SEQ ID NO:1).

9. The method of claim 1, wherein the promoter sequence is the 2451 bp upstream of the transcription start site (nucleotides 1077 to 3527 of SEQ ID NO:1).

10. The method of claim 1, wherein the promoter sequence is the 1987 bp upstream of the transcription start site (nucleotides 1541 to 3527 of SEQ ID NO:1).

11. The method of claim 1, wherein the promoter sequence is the 1426 bp upstream of the transcription start site (nucleotides 2102 to 3527 of SEQ ID NO:1).

12. The method of claim 1, wherein the promoter sequence is the 931 bp upstream of the transcription start site (nucleotides 2597 to 3527 of SEQ ID NO:1).

13. The method of claim 1, wherein the promoter sequence is the 533 bp upstream of the transcription start site (nucleotides 2995 to 3527 of SEQ ID NO:1).

14. The method of claim 1, wherein the promoter sequence is the 380 bp upstream of the transcription start site (nucleotides 3148 to 3527 of SEQ ID NO:1).

15. The method of claim 1, wherein the promoter sequence is the 195 bp upstream of the transcription start site (nucleotides 3333 to 3527 of SEQ ID NO:1).

* * * * *